(12) United States Patent
Perkins et al.

(10) Patent No.: US 7,993,413 B2
(45) Date of Patent: Aug. 9, 2011

(54) VALVE SYSTEM FOR PROSTHETICS

(76) Inventors: Matt Perkins, Boise, ID (US); Dale Perkins, Twin Falls, ID (US)

( * ) Notice: Subject to any disclaimer, the term of this patent is extended or adjusted under 35 U.S.C. 154(b) by 16 days.

(21) Appl. No.: 12/364,511

(22) Filed: Feb. 2, 2009

(65) Prior Publication Data

US 2009/0198346 A1 Aug. 6, 2009

Related U.S. Application Data

(63) Continuation-in-part of application No. 11/527,752, filed on Sep. 25, 2006, now abandoned.

(60) Provisional application No. 61/024,913, filed on Jan. 31, 2008, provisional application No. 60/719,785, filed on Sep. 24, 2005.

(51) Int. Cl.
*A61F 2/60* (2006.01)
*F16K 25/00* (2006.01)

(52) U.S. Cl. ......................................... 623/34; 251/285

(58) Field of Classification Search .................... 623/33, 623/37, 34
See application file for complete search history.

(56) References Cited

U.S. PATENT DOCUMENTS

| | | |
|---|---|---|
| 1,586,015 A | 1/1926 | Underwood |
| 2,530,285 A | 12/1947 | Catranis |
| 2,533,404 A | 8/1948 | Sharp et al. |
| 2,790,180 A | 11/1955 | Hauser |
| 4,010,052 A | 3/1977 | Edwards |
| 4,106,745 A | 8/1978 | Carrow |
| 4,655,779 A | 4/1987 | Janowiak |
| 5,007,937 A | 4/1991 | Fishman et al. |
| 5,201,774 A | 4/1993 | Greene |
| 5,490,537 A | 2/1996 | Hill |
| 5,658,353 A | 8/1997 | Layton |
| 5,709,017 A | 1/1998 | Hill |
| 5,807,303 A | 9/1998 | Bays |
| 6,287,345 B1 | 9/2001 | Slemker et al. |
| 6,334,876 B1 | 1/2002 | Perkins |
| 6,361,568 B1 | 3/2002 | Hoerner |
| 6,508,842 B1 | 1/2003 | Caspers |
| 6,544,292 B1 | 4/2003 | Laghi |
| 6,626,952 B2 | 9/2003 | Janusson et al. |
| 6,706,364 B2 | 3/2004 | Janusson et al. |
| 6,761,742 B2 | 7/2004 | Caspers |
| 6,797,008 B1 | 9/2004 | Arbogast et al. |
| 7,448,407 B2 * | 11/2008 | Alley et al. ................... 137/543 |
| 2004/0181290 A1 | 9/2004 | Caspers |
| 2004/0260403 A1 | 12/2004 | Patterson et al. |
| 2007/0112440 A1 | 5/2007 | Perkins et al. |

* cited by examiner

*Primary Examiner* — Bruce E Snow
*Assistant Examiner* — Melissa Hoban
(74) *Attorney, Agent, or Firm* — Pedersen and Company, PLLC; Ken J. Pedersen; Barbara S. Pedersen

(57) ABSTRACT

A valve system regulates the air pressure in the space(s) between a residual limb, or liner-covered limb, and a hard socket of an external prosthesis, and may include a manually-controlled air outlet and inlet valve on a distal region of a hard socket, and/or an automatic one-way outlet valve. The manually-controlled valve is opened and closed by partial rotation/twisting of a handle portion, which creates slight separation of the handle and base portions through which may pass air. The handle and base are prevented from becoming entirely separated during normal use by a snap-fit of the base onto the handle that retains the ability of the handle and base to rotate relative to each other by means of a ramp system, and a stop(s) that limit(s) the amount of relative rotation of the handle and base portions of the valve.

13 Claims, 9 Drawing Sheets

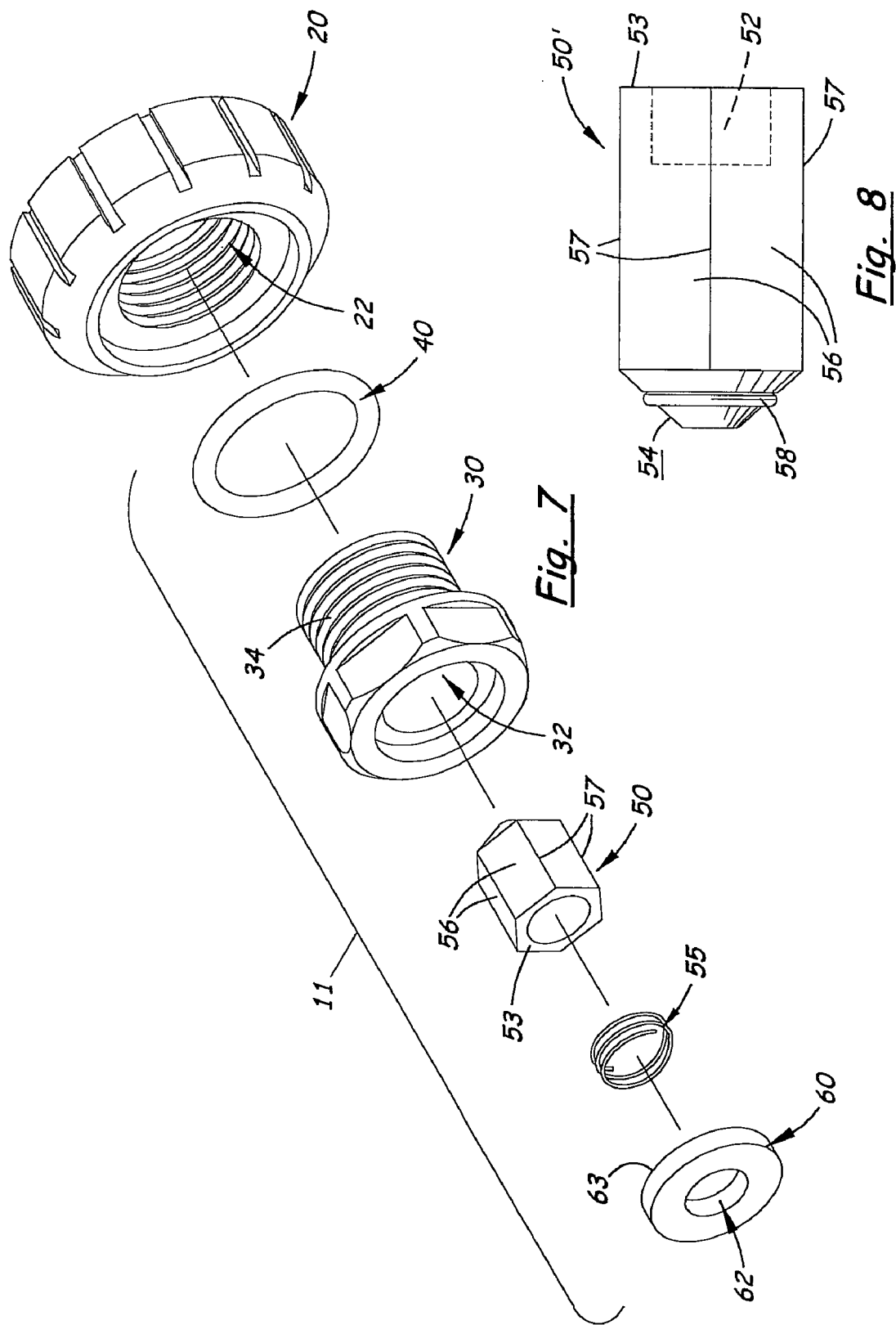

VALVE SYSTEM FOR PROSTHETICS

This application claims benefit of provisional application Ser. No. 61/024,913, filed Jan. 31, 2008, and is a continuation-in-part of non-provisional application Ser. No. 11/527,752, filed Sep. 25, 2006, which claims benefit of provisional application Ser. No. 60/719,785, filed Sep. 24, 2005, the entire disclosures of all of these applications being incorporated herein by this reference.

BACKGROUND OF THE INVENTION

1. Field of the Invention

The present invention relates to prosthetics, and more specifically to a valve system for air release from an external prosthetic such as may be used on a residual limb.

2. Related Art

Gravitational and other forces tend to cause separation between a prosthetic limb and a residual limb. This happens, for example, during the swing phase of the gait, when a prosthetic leg is additionally subjected to centrifugal forces. The manner in which an artificial limb is suspended and/or attached to the residual limb determines the amount of control an amputee has over the prosthesis. Patients have routinely worn a variety of belts, straps, cuffs and harnesses to prevent the prosthetic limb from separating from the residual limb, but such devices are inconvenient and tend to cause chafing against the patient's body, giving rise to sores and abrasions.

It has long been appreciated that differential air pressure, often referred by those of skill in the art as "suction," may be utilized to retain or suspend, or assist in retaining or suspending, a prosthetic limb on a patient's residual limb. "Suction suspension" typically involves a hard socket and a cooperating liner positioned between the residual limb and the prosthetic socket. The liner is rolled onto the residual limb for a suction, slight compression, and/or gripping connection of the inner gel layer (or otherwise tacky layer) of the liner to the skin of the residual limb. The liner-covered limb is then inserted into the prosthetic socket, and the outer surface/layer of the liner preferably forms a suction, grip, or other interference fit to the socket to interfere with the socket falling off the limb.

Said "suction" fit between the liner and the socket, due to the material and texture of today's preferred liner as further discussed below, may more accurately be referred to as a "partial-suction" fit. In such a "partial-suction" fit, the outer surface of the liner and its close fit with the interior surface of the socket will provide significant resistance to air entering the socket from outside the socket (via the top opening of the socket). Still, because today's preferred liners do not form a true air-tight seal with the socket, some air will slowly enter the socket, especially during the swing portion of the wearer's gait and during periods of relative inactivity.

Socket liners frequently have been called "suction liners," "gel liners," "roll-on liners" or "suspension liners" and include the "first generation" of gel-layer-only liners, and also the modern "second generation" liners currently preferred by most wearers of prosthetics. These modern liners "second generation" liners typically comprise a thin textile/fabric outer layer that is fixed to the gel-like inside layer. Thus, the second generation of liners is similar to the first generation in its connection to the residual limb, but its connection to, or cooperation with, the socket is modified by the presence of the textile/fabric layer. The term "suction liner" began with the first generation liners, which featured the gel layer contacting both the residual limb (liner's inner surface) and the socket (liner's outer surface), and which, therefore, could be used to create a fairly high amount of pressure differential between the inside of the socket (in the "well" of the socket) and the surrounding ambient air. The terms "suction liner" and "suction socket" are still used by many manufacturers, prosthetic technicians, insurance and medicare/medicaid entities, and wearers of prosthetics, even though the modern liners, with their textile/fabric outer layers, typically do not form what would be called "true" or "pure" suction with the socket, as further discussed below. See the discussion of suction liners in Janusson, et al. (U.S. Pat. No. 6,706,364) and Janusson, et al. (U.S. Pat. No. 6,626,952).

Preferred socket liners are usually fabricated from silicone, urethane, or other gel-like material that grips the limb to such an extent that they need to be rolled-onto the limb from a rolled-up "doughnut" form, rather than pulled on like a sock. When rolled-on, there is little, if any, air remaining between the inner surface of the roll-on liner and the limb, and the roll-on liner is snug against the limb all the way around the circumference of the limb. Also, the inner surface of the roll-on liner is of such material and tacky texture that air will not be able to, or be very unlikely to, enter between the roll-on liner and limb. Thus, the roll-on liner may be said to form a suction fit and/or a slight compression fit with the limb. A distal force on the liner, such as caused by the swing of a gait with a prosthetic leg, may tug on the roll-on liner but typically does not loosen, lower, or remove the liner from the limb.

The hard socket is usually laminated or otherwise fabricated from polyethylene, polypropylene, or other copolymers, for example, and is donned over the liner and the residual limb. A suction-fit, including a partial-suction fit, as discussed above, may form between the liner-sheathed limb and the interior of the socket. A "true" suction fit (allowing high suction, greater amount of vacuum) will be more likely to form if the liner exterior surface is smooth and flexible enough to conform to the contours of the residual limb, for example, non-air-permeable material such as the silicone, urethane, or other rubbery or gel-like material such as described above for the liner-to-limb connection; if the interior surface of the socket is also smooth and non-air-permeable; and, of course, if the socket has no un-sealed holes or apertures.

A "partial" suction fit (allowing lower suction, low amount of vacuum) is more likely to form if one of these conditions is not met, for example, if the outside of the liner is the thin fabric or other woven material bonded to a rubbery/gel-like interior layer of the liner, for example, as described above for "second generation" liners. In such a case, some air will tend to leak through or past the fabric layer of the modern liners into the well of the socket, that is, between the liner and the socket interior surface, so that there is typically not a true air-tight seal between the two. However, the air leaks fairly slowly because of the preferred close fit between the contour of the liner-cover limb and the contour of the internal surface of the socket. This slow air leakage and close fit typically allow their to be a "partial" suction fit between the socket and the liner outer surface, and this "partial" suction fit tends to be more comfortable for many wearers that a "true" or "full" suction fit. In other words, a textile/fabric-covered liner and the resulting "partial" suction tends to be more comfortable than the stronger "tugging" on the residual limb created by the "full" suction of first generation, gel-layer-only liner. The air that slowly leaks into space(s) in between the socket and the liner tends to be expelled with each step due to the force of the residual limb pushing into the socket. This way, modern, fabric-covered roll-on liners still tend to create some pressure differential between the well of the socket and the ambient air.

Therefore, many of skill in the field of prosthetics still apply the term "suction" to a fit or suspension of the prosthetic to the limb ranging from excellent suction (with a "true" seal, large resistance to equalization of pressure between the inside and the outside of the socket) to slight suction (with a "partial" seal, small resistance to said equalization such as in many popular liners). Therefore, the terms "suction," "suction-fit," and "suction suspension" herein are therefore not limiting to a particular amount of pressure differential, but to the general process known well in this field of providing a "roll-on" liner or other "interference" liner that helps keep a socket on a residual limb while creating at least a small amount of blockage/hindrance to air freely moving in and out of the socket well past the residual limb.

Therefore, it may be said that any region or amount of negative pressure in the space(s) between the liner-sheathed stump and the interior of the socket, relative to ambient (outside of the socket), may help to hold the prosthesis upon the limb during use. Certainly, more suction is more secure than slight suction, but there may be comfort sacrifices that result from more suction, for example, chaffing or pulling on the limb. A high-suction prosthesis suspension system may cause the user a discomforting disturbance of circulation in the limb on which the prosthesis is worn, due to the build up of a high degree of partial vacuum during walking, particularly in warm humid weather. Therefore, a very popular conventional roll-on liner is one such as the Ohio Willow Wood Alpha™ liner, which has multiple layers, that is, a rubbery/gel-like inner layer and a thin fabric outer layer bonded to the inner layer, so as to moderate the suction to a reasonably effective amount without allowing the great forces on the limb that can result from a high amount of suction. A "suction liner" or "roll-on liner" suspension, even in moderate range of suction provided by the preferred liners, gives the patient the ability to better control the prosthesis and provides for useful sensory or proprioceptive feedback. This is because there is a more intimate connection between the limb and the prosthetic, over much of the surface area of the limb, compared to old-fashioned waist belts, distal locks, or other methods. Suction or roll-on liner suspension also make a prosthesis feel lighter as compared to other forms of suspension.

A valve system may be used in combination with a suction/roll-on suspension system in order to regulate the air pressure in the socket, so that undesirable pressure differentials do not prevent or complicate the donning and doffing of the socket. Conventional valves aim at relieving buildup of pressure when the lined limb is inserted into the socket, which is typically a snug fit by design, to prevent a positive pressure inside the socket relative to outside of the socket (ambient air) and therefore to allow donning.

Because the typical valve system is a one-way valve, or "check valve" that only allows air to be expelled from the socket, it is intended to maintain a slight negative pressure (slight, partial suction) relative to ambient once the socket has been fitted on the residual limb and used. The process of walking and other weight-bearing will tend to push the limb further into the socket, but the swing portion of the gait will tend to pull the socket off the limb. The pushing of the limb further into the socket may cause the valve to allow air to be expelled, and the pulling of the socket during the swing portion of the gait will tend to create suction in the socket because the valve will not allow air to enter the socket through the valve.

In applications wherein the multi-layer roll-on liner allows air to slowly leak into the socket well, as discussed above, or wherein a seam, connection, lock or other aperture in the socket allows air to leak into the socket, weight-bearing steps will tend to expel air from inside the socket through the valve and then said leaking will tend to replace at least some of it (especially on the swing of the gait). Therefore, there may be frequent opening and closing of the valve, perhaps for each, or for many, of the user's steps. Many conventional valves for these applications are known to either not work very well, to plug easily, or to make embarrassing noise with each step as the air is expelled.

There are many valve systems in use in the market. Typical valve systems use an inner base that passes from the inside of the socket to the outside of the socket. The outer housing and the valve are then threaded onto the inner base or threaded to the socket wall in an attempt to create an air-tight seal between the valve and the socket wall. Such systems require a generally flat socket wall surface for installing the valve and outer housing to prevent air from leaking out of the socket around the outer housing instead of being expelled through the valve at the desired air pressure determined by the one-way valve structure.

Issued patents and patent publications relating to valve systems are listed as follows: Underwood (U.S. Pat. No. 1,586,015), Catranis (U.S. Pat. No. 2,530,285), Sharp et al. (U.S. Pat. No. 2,533,404), Hauser (U.S. Pat. No. 2,790,180), Edwards (U.S. Pat. No. 4,010,052), Carrow (U.S. Pat. No. 4,106,745), Greene (U.S. Pat. No. 5,201,774), Hill (U.S. Pat. No. 5,490,537), Hill (U.S. Pat. No. 5,709,017), Slemker et al. (U.S. Pat. No. 6,287,345), Perkins (U.S. Pat. No. 6,334,876), Hoerner (U.S. Pat. No. 6,361,568), Caspers (U.S. Pat. No. 6,508,842), Laghi (U.S. Pat. No. 6,544,292), Caspers (U.S. Pat. No. 6,761,742), Abrogast et al. (U.S. Pat. No. 6,797,008), Caspers (U.S. Publication No. 2004/0181290), and Patterson et al. (U.S. Publication No. 2004/0260403).

SUMMARY OF THE INVENTION

The present invention is a valve system for helping to regulate the air pressure in the space(s) between a residual limb, or liner-covered limb, and a hard socket of an external prosthesis. The valve system may be used to regulate said air pressure for improved donning and doffing the prosthesis, and/or during walking and other normal use of the prosthesis.

The preferred valve system comprises a manually-controlled air outlet and inlet valve that may be installed on a distal region of a hard socket, and/or an automatic one-way outlet valve. The manually-controlled valve may be used to open the socket well to the outside air by providing an air passage from a distal region of the socket well, so that, when the wearer inserts his/her residual limb into the socket, air is pushed out through the manual valve rather than building up pressure inside the socket. Also, when a user wishes to doff the prosthetic, he/she may manually open the valve to allow air to flow through the valve into the socket, equalizing the air pressure inside and outside the socket, for easier removal of the limb.

The manually-controlled air outlet and inlet valve is preferably opened and closed by twisting of a handle portion of the valve system, wherein partial rotation of the handle portion relative to the base portion of the valve system creates slight separation of the handle and base portions to form a gap through which may pass air from the well of the socket. This simple twisting, or partial rotation, allows sure and repeatable control of the valve wherein the valve stays in either the open or closed position without the user's hand holding the valve in that position. Thus, after opening the manual valve, the valve stays in hands-free open status, while the wearer may use his/her hands to don or doff the prosthesis. The manual valve preferably comprises a system for preventing the handle and base from becoming entirely separated during normal use, so that the handle portion does not fall off of the prosthesis. Also, the manual valve preferably comprises a stop (s) that limit(s) the amount of relative rotation of the handle and base portions of the valve, so that the user need only rotate the handle a small amount, for example, less than 90 degrees, to affect opening or closing the valve. The stop(s) may be part of the system for preventing the handle and base from entirely separating, or may be provided in addition to said system for preventing.

In one embodiment, the valve system comprises only said manual valve, while in another embodiment, the valve system comprises both a manual valve and also an automatic one-way air outlet valve. In yet another, less-preferred embodiment, the valve system may comprise only the automatic one-way air outlet valve.

In embodiments comprising the automatic air outlet valve, said automatic valve is a "one-way" or "check" valve, with a valve stem that "pops" or otherwise opens consistently and quietly at a small differential pressure, for example, a pressure inside the socket (in the distal space(s) between said socket and the limb or liner-covered limb) that is ≦3 psi pressure above ambient pressure (outside the socket).

The valve system, whether it includes only a manual valve, both manual and automatic valves, or only an automatic valve, are preferably adhesively mounted on the outside of the socket. Thus, the valve system is easier to mount than conventional valves due to this preferred adhesive mounting and due to preferably no part of the valve being installed from the inside of the socket. The preferred valve system has no threaded attachment to the socket, and no portion that extends into the hard socket. The preferred valve system comprises a base portion that is installed on or near the outside surface of the hard socket, preferably without threaded connection between the base and the hard socket. A hole is drilled in the hard socket from the outside surface of the socket to the inside surface of the socket, to align the hole in the socket with the bores/passages in the valve system. The other portions of the valve system, for example, the handle and the optional one-way valve structure, are then connected to the base portion, without said other portions requiring any contact with, or direct attachment to, the hard socket. Said other portions may be removable for cleaning, replacement of o-rings or other seals, and/or for other maintenance without removing the base from the hard socket.

The inventors envision, however, that features of the invented valve system may also be incorporated into a valve that is attached to a hard socket by other means than are discussed herein as being preferred. For example, conventional mounting systems for air expulsion valve in the industry, as discussed in the Related Art section above, may allow a valve with some of the invented features of the present invention to be used in a format wherein the valve is connected to a base that protrudes or resides inside the hard socket.

In embodiments comprising a one-way air outlet valve, the one-way valve stem may have a polygonal side wall, or have other recesses or grooves in its side wall(s) to create passages through which air may flow quietly. Alternatively, the valve stem may be cylindrical and the channel in which the valve stem slides (the valve housing bore) may be polygonal or have recesses or grooves in its wall(s), to create passage through which air may flow quietly. Or, both valve stem and the housing bore may be non-cylindrical. The preferred low-profile, external-mounting of the valve, and the quieter action of, and quieter air flow from, the one-way valve as it "pops" and expels air frequently during walking, may result in a less intrusive and less noticeable apparatus than is more acceptable and less embarrassing to wearers.

BRIEF DESCRIPTION OF THE DRAWINGS

FIG. 7 is an exploded perspective view of the valve embodiment shown in FIGS. 1-6.

FIG. 8 is an alternative embodiment of a valve stem that may be used in the embodiment of FIGS. 1-7 and that has an o-ring in its end surface.

In FIG. 9, the one-way outlet valve is shown in the closed position, which means that the pressure inside the socket well has not reached a level above the ambient pressure that caused the valve stem to move outward and open the one-way valve passage. In FIG. 9, the manual valve is in the closed position.

In FIG. 18, the external ramps of the handle portion are shown (the one near the viewer in solid lines and the one hidden from view in dashed lines) and the cooperating bore and internal ramps of the base portion are shown in dashed lines.

DESCRIPTION OF THE PREFERRED EMBODIMENTS

Figure 9:
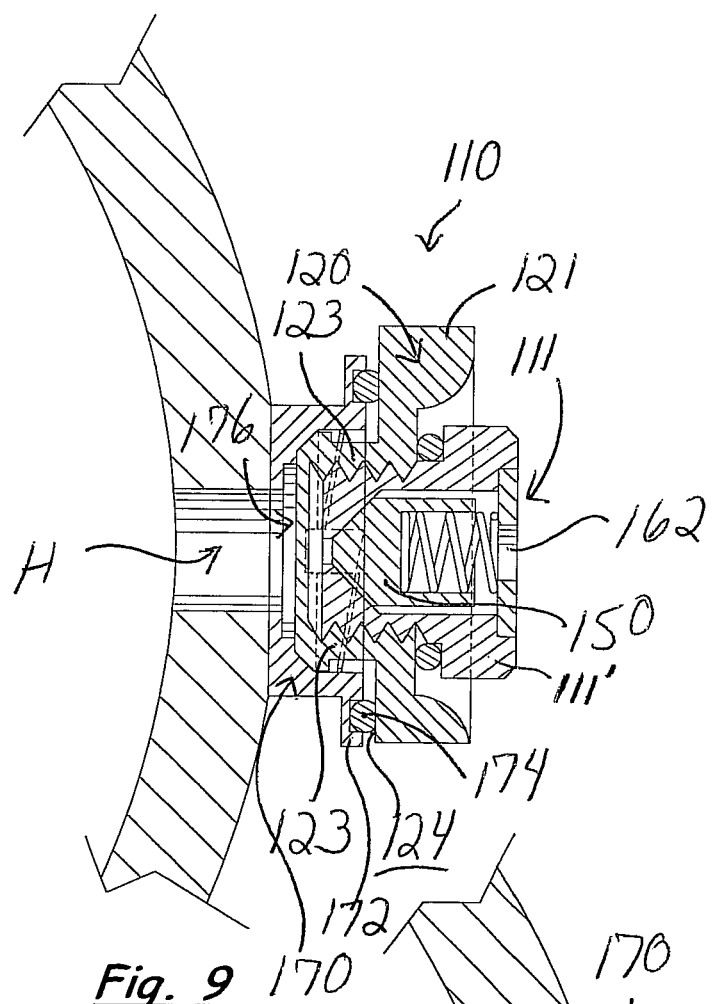
FIG. 9 is a cross-sectional view of an alternative embodiment of valve system, installed on a hard socket exterior surface over a hole, wherein the valve system comprises a one-way outlet valve similar to the embodiment of FIGS. 1-7 and also comprises one embodiment of the invented manual air inlet and outlet valve.
Figure 10:
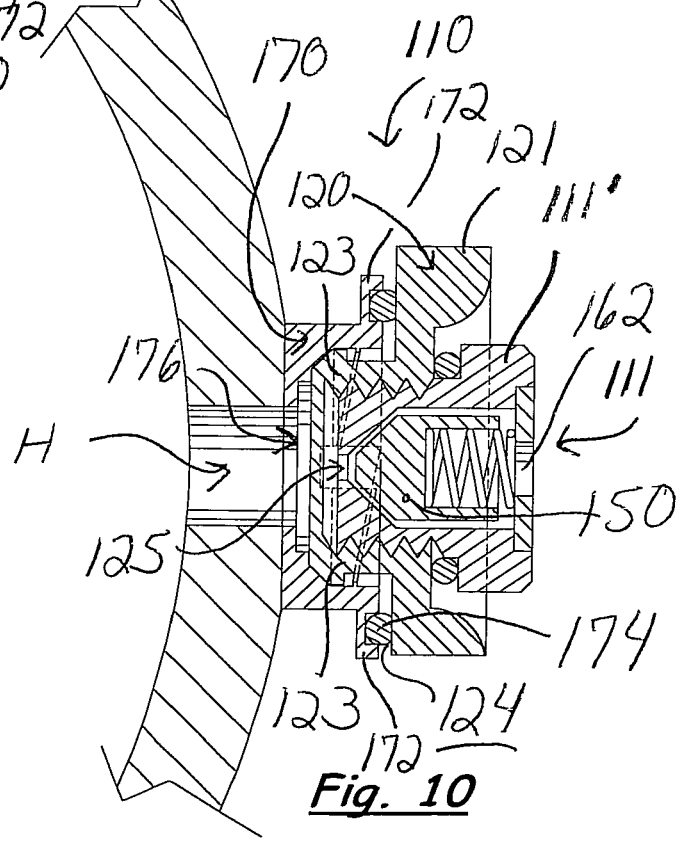
FIG. 10 is a cross-sectional view of the embodiment of FIG. 9, wherein the manual valve is still in the closed position, but the one-way outlet valve has opened to allow expulsion of air from the socket well.
Figure 11:
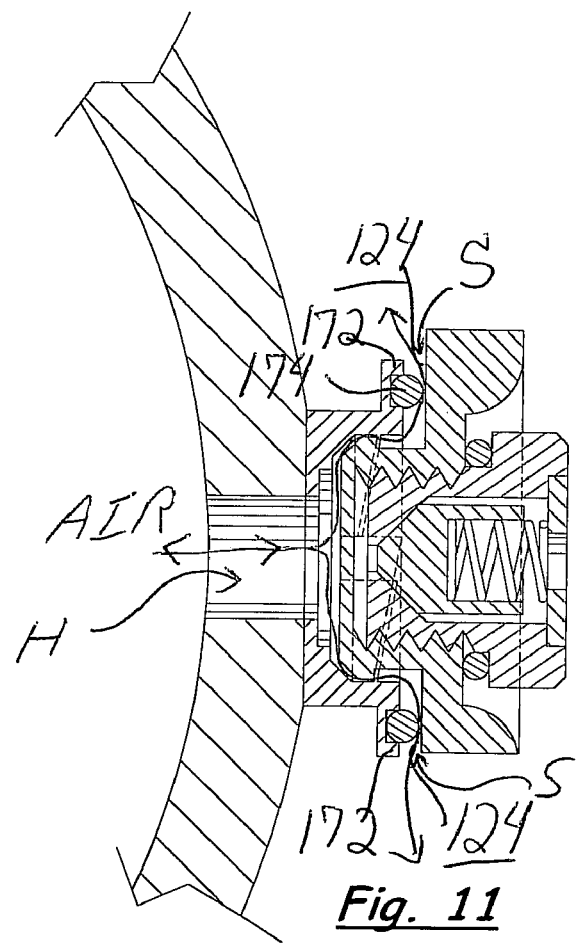
FIG. 11 is a cross-sectional view of the embodiment of FIGS. 9 and 10, wherein the one-way valve is in the closed position, but the manual valve has been opened, by turning/rotating the handle portion relative to the base portion, so that air may enter or exit the hard socket well from a passageway between said handle portion and said base portion.
Figures 12, 13:
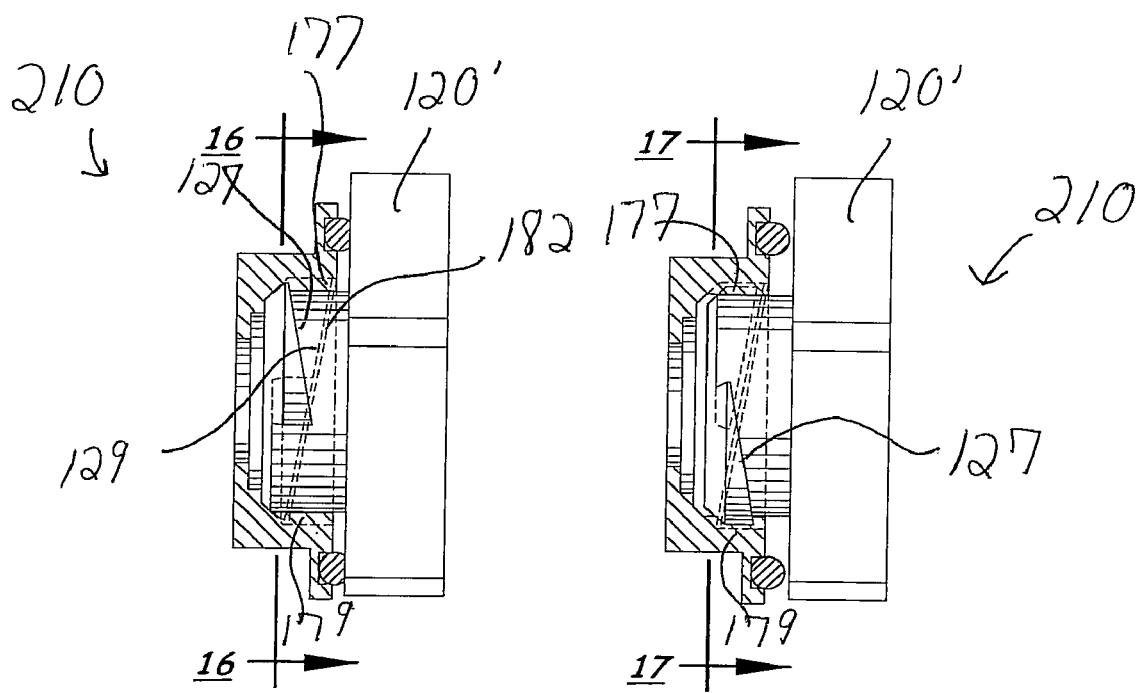
FIG. 12 is a side view of the embodiment of FIGS. 9-11, removed from the hard socket, wherein the base portion is shown in cross-section and the manual valve is shown closed and the one-way valve is hidden inside the handle portion.
FIG. 13 is a side view of the embodiment of FIGS. 9-12, removed from the hard socket, wherein the base portion is shown in cross-section and the manual valve is opened, and the one-way valve is hidden inside the handle portion.
Figure 14:
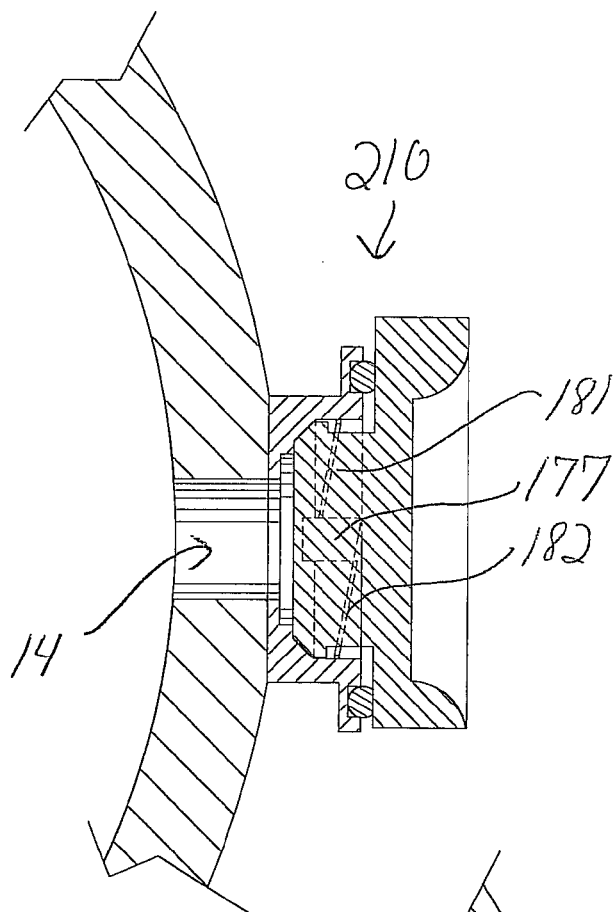
FIG. 14 is a cross-sectional view of an alternative embodiment of the invented valve system installed on a hard socket wall over a hole, which valve system comprises a manual valve in the closed position and which does not comprise a one-way inlet and outlet valve.
Figure 15:
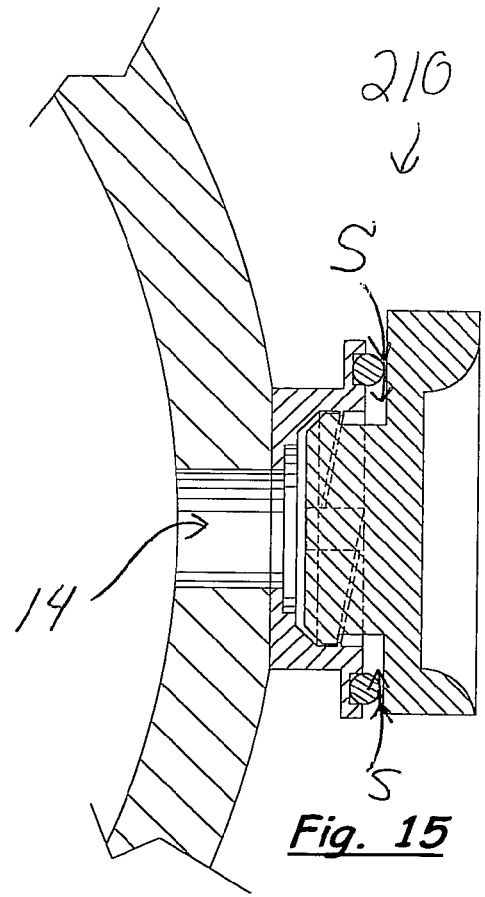
FIG. 15 is a cross-sectional view of the embodiment of FIG. 14, wherein the handle portion has been turned/rotated to open the manual valve, so that air may enter or exit the hard socket well from a passageway between said handle portion and said base portion.
Figure 16:
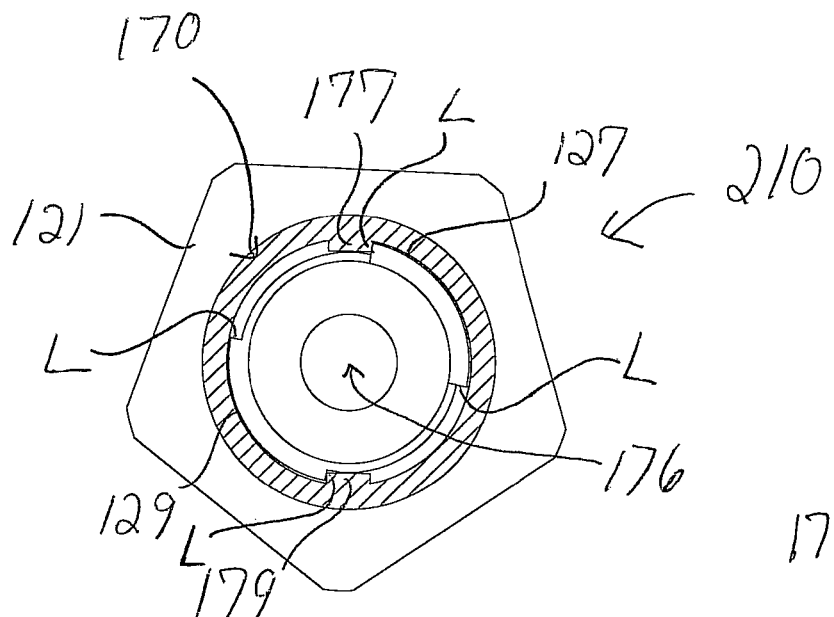
FIG. 16 is a cross-sectional view of the embodiment of FIG. 12, viewed along the line 16-16 in FIG. 12, this cross-section portraying positions of tabs and ramps in a position wherein the manual valve is closed.
Figure 17:
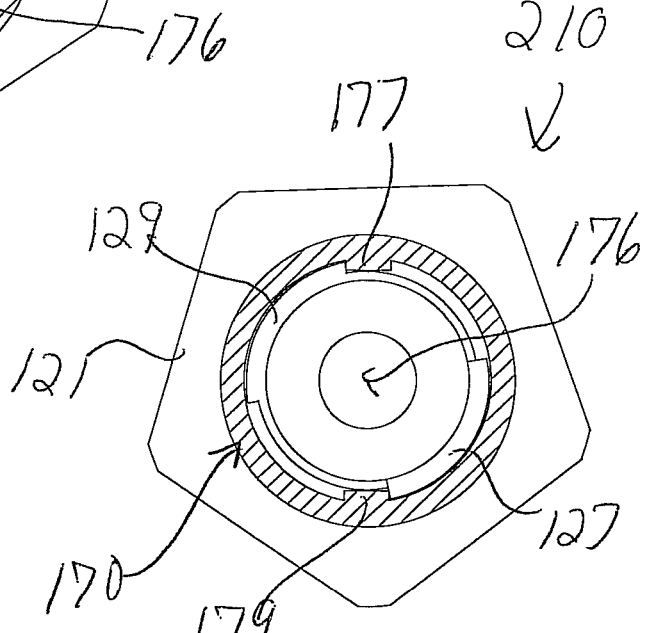
FIG. 17 is a cross-sectional view of the embodiment of FIGS. 12 and 13, viewed along the line 17-17 in FIG. 13, this cross-section portraying positions of tabs and ramps in a position wherein the manual valve is closed.
Figure 18:
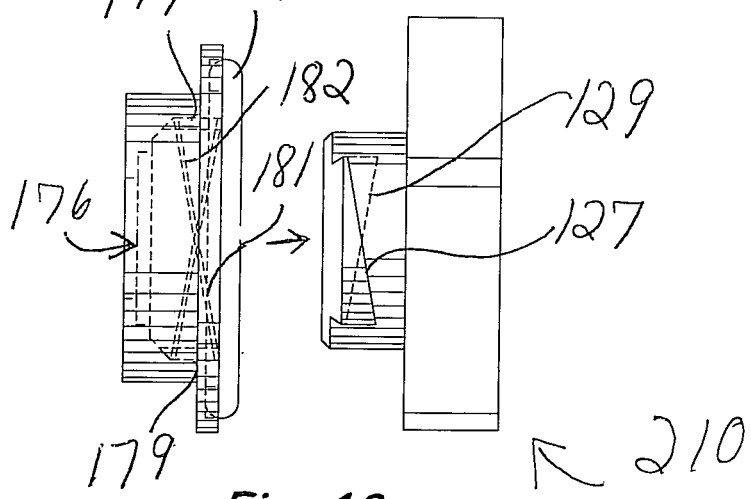
FIG. 18 is a side view of the embodiment of FIGS. 14 and 15, with the handle portion separated from the base portion.

In the Figures, there are shown several, but not the only, embodiments of the preferred valve system for prosthetics. FIGS. 1-8 illustrate an embodiment having only a one-way air outlet valve. FIGS. 9-11 illustrate an embodiment having both a one-way air outlet valve and an embodiment of a manual valve. FIGS. 12-18 illustrate an embodiment that having only an embodiment of a manual valve.

Referring to embodiments that include a one-way air outlet valve, it will be understood by one of skill in the art after reading this application and viewing the drawings, that, once the air pressure inside the hard socket (relative to the ambient pressure outside the socket) exceeds the crack pressure of the one-way valve, the invented one-way or "check" valve opens and air is expelled out through the valve. This is useful during donning of the socket, as the insertion of the limb, or liner-covered limb, increases pressure in the socket well; the one-way valve system opens to generally equalize the ambient pressure and the pressure inside the socket in order to allow the donning.

After donning, when the wearer takes each step, pressure is exerted downward on the limb, that is, toward the bottom of the socket well, and this also increases the pressure inside the socket well. Again, the preferred one-way valve will "crack" or "pop" to relieve this pressure, and then close when the pressure is generally equalized by cessation of the downward pressure of the step, and/or when the swing phase of the gait suspends the prosthetic from the residual limb/liner and a slight suction/vacuum (relative to the ambient pressure) tends to be created in the socket. The preferred valve is designed with a "crack pressure" in the range of ≦3 psi differential, and more preferably 1-3 psi, or most preferably 1-2 psi, differential, so that, with this slight suction/vacuum, and preferably with any pressure differential below the "set-point" (selected from the range of 1-3, or 1-2, psi positive pressure inside the socket well, that is, 1-3 or 1-2 psi above the ambient pressure outside the socket well), the valve will close to not allow air into the socket through the one-way valve.

Figure 1:
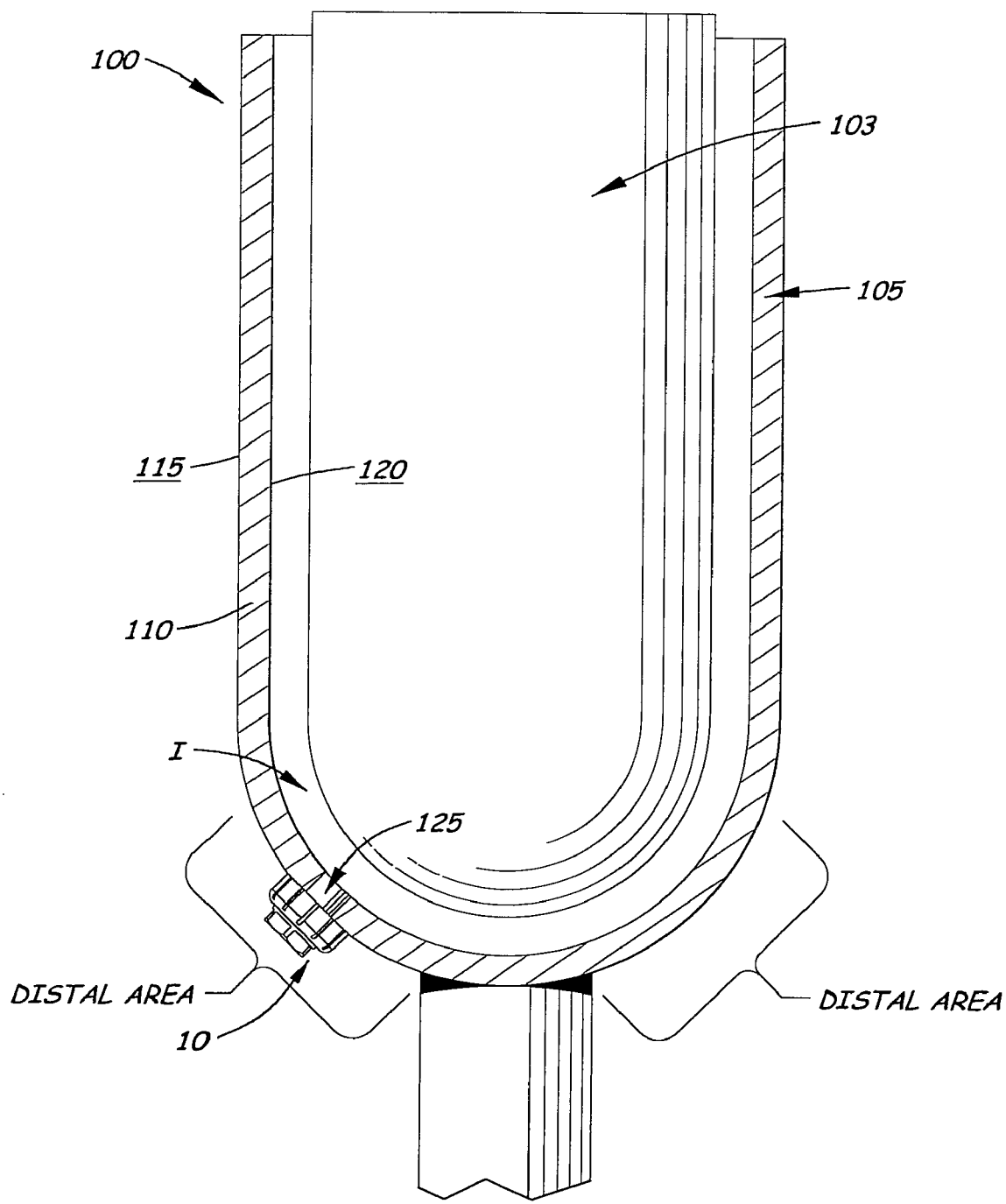
FIG. 1 is a schematic view of a hard socket and liner combination, wherein one embodiment of the invented valve is shown attached to the outside of the hard socket. In this view, the liner is shown as spaced from the socket, but it will be understood from the foregoing discussion, that the liner and socket will tend to be in close contact for at least part of the length along the socket and preferably all around the circumference of the liner and socket at or near the top (proximal region) of the socket. Some space between the liner-covered limb distal end and the socket interior surface distal end is normally present, so that the limb does not reach all the way to the distal end of the well of the socket.

Valve system 10 is adapted to cooperate with a suspension system 100 for external prosthetic devices, which, as discussed in the Related Art section, preferably include a liner that provides at least some blockage/hindrance to air passing between the socket and the liner. As shown in FIG. 1, the preferred suspension system 100 comprises a liner 103 received on a residual limb, and a hard socket 105 adapted to fit over the liner 103 and residual limb. The hard socket 105 comprises a sidewall 110 defining an interior space I, wherein the sidewall 110 comprises an outer surface 115 and an inner surface 120.

The liner 103 is preferably a roll-on liner, and may be of various types, as discussed in the Related Art section, which provide varying amounts of "suction." Modern liners comprising both an inner gel layer and a textile/fabric outer layer are preferred, and the preferred valve system of the invention cooperates well with these liners. The valve system embodiments comprising a one-way air outlet valve are specially adapted to allow air to be expelled quietly and consistently, even as often as every step, as may be desired with the amounts of air "leakage" experienced with fabric-covered liners.

As shown in FIGS. 2-7, valve system 10 comprises a base 20 having an internally threaded circular bore 22 extending through the base 20. The base 20 is generally cylindrical in shape and is preferably fabricated from a durable polymeric material or "plastic." Alternatively, the base 20 may not comprise threads, but may instead have other adaptation for joining to the one-way valve assembly that is inserted and secured to the base. For example, a bayonet or other latching mechanism that anchors or secures the valve assembly into the base may be used.

Figure 1B:
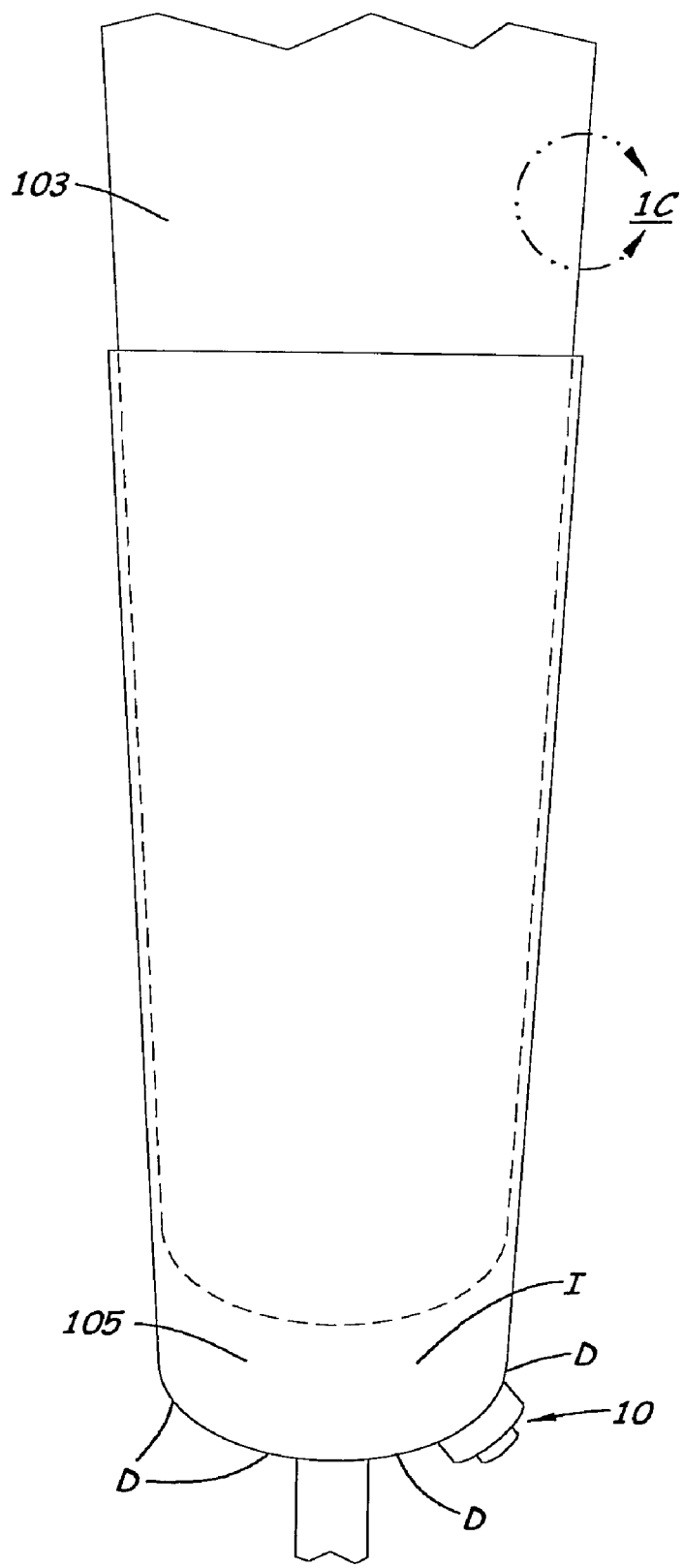
FIG. 1B is a schematic view of a hard socket holding a residual limb with second generation roll-on liner, with one embodiment of the invented valve system installed on the hard socket distal portion. This view illustrates more accurately the preferred relationship of residual limb, roll-on liner, socket and valve.
Figure 1C:
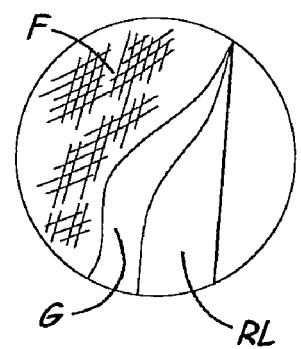
FIG. 1C is a schematic cross-section detail view of a two-layer liner on a residual limb RL, such as in FIG. 1B, wherein the liner has an inner gel-layer G that contacts the residual limb RL and an outer fabric layer F that adhered to the gel-layer G.
Figure 2:
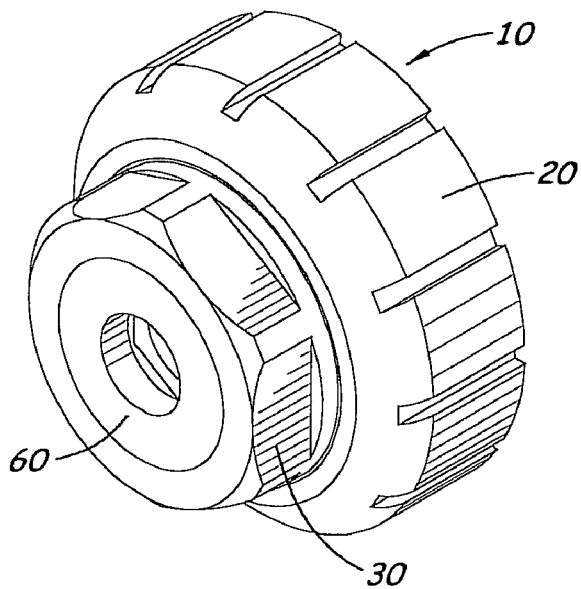
FIG. 2 is a front perspective view of the valve embodiment of FIG. 1, which valve embodiment comprises a one-way air outlet valve but not a manual air inlet and outlet valve.
Figure 3:
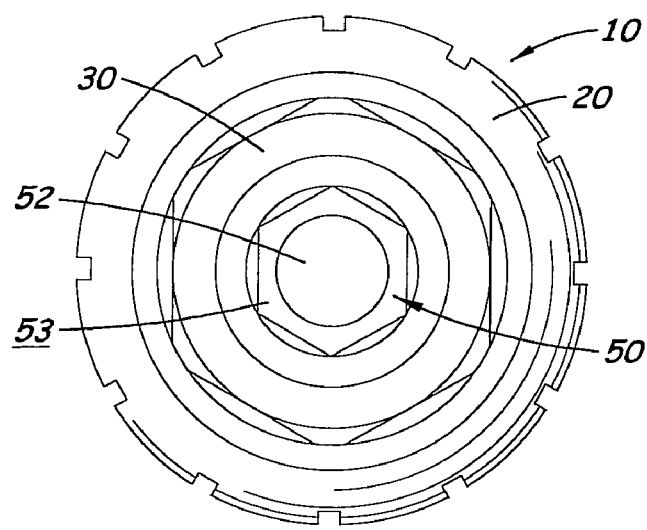
FIG. 3 is a front view of the valve embodiment shown in FIGS. 1 and 2, with a front cover, o-ring/gasket, and spring removed to better show internals of the valve.
Figure 4:
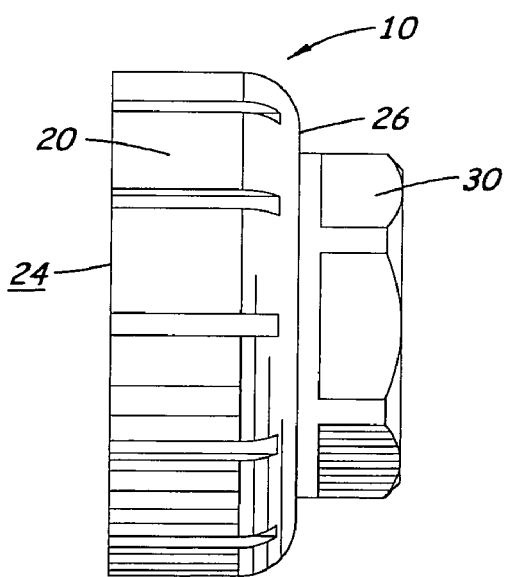
FIG. 4 is a side view of the valve embodiment shown in FIGS. 1-3.
Figure 5:
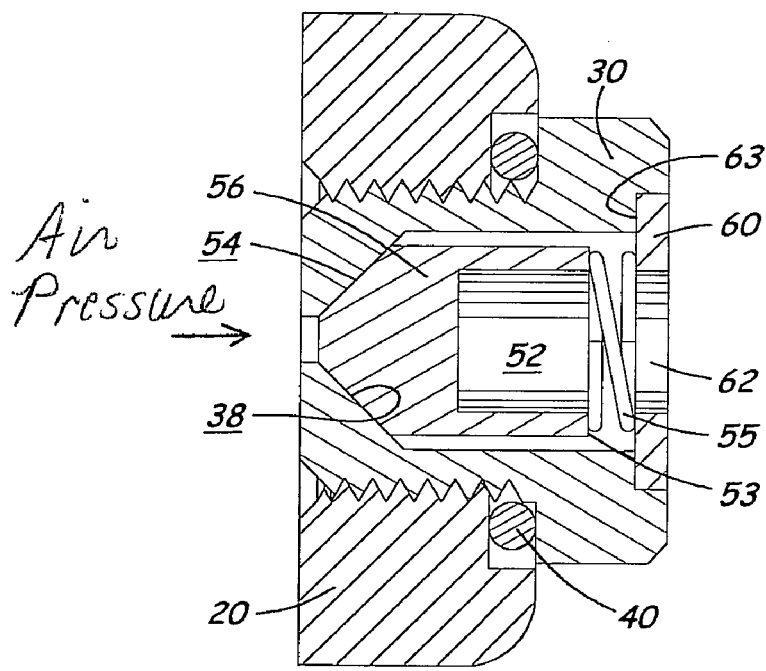
FIG. 5 is a cross-sectional side view of the embodiment shown in FIGS. 1-4, and the valve is shown in the closed position.
Figure 6:
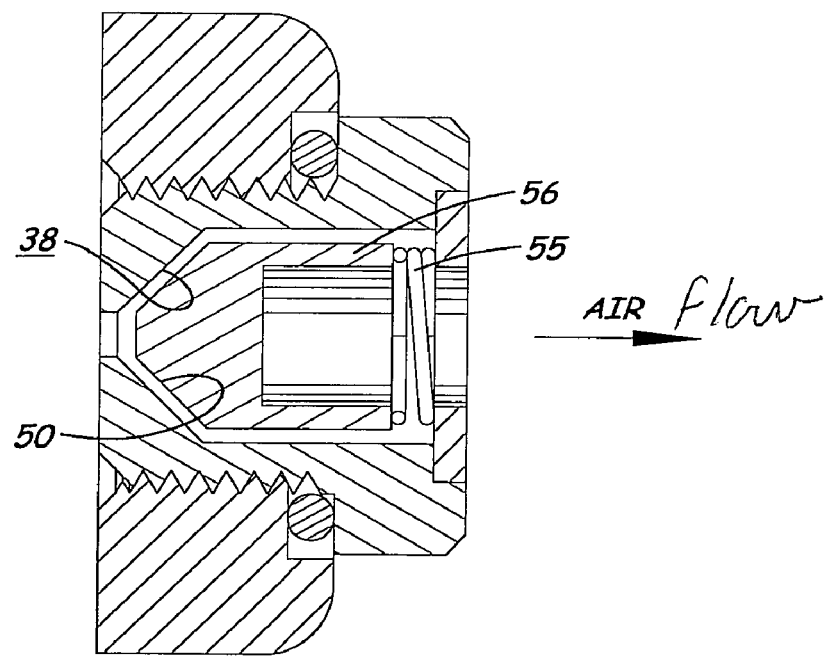
FIG. 6 is a cross-sectional side view of the embodiment shown in FIGS. 1-5, wherein the valve is shown in the open position allowing air to be expelled.

The base 20 has a generally flat bottom portion 24 and a slightly curved or rounded top portion 26 (see FIG. 4). The bottom 24 of the base 20 may be slightly concave to mimic the contour of the outer surface 115 of the socket in the preferred distal installation area on the socket. See FIGS. 1 and 1B, wherein the region labeled as "Distal Area" (or D) is indicative of the preferred, but not the only, region for attachment of the invented valve system. Distal attachment is preferred, wherein "distal" broadly refers to attachment of the valve system to the socket in a region below where the lower-most end of the residual limb will reach in the socket during use. Distal attachment of the valve system, however, preferably does not include attachment of the valve system at the bottom-most point of the socket, as this location is occupied by the post leading to the prosthetic foot and/or a distal lock that connects to the lower-most end of the residual limb.

With the valve system 10 placed on a distal area of the hard socket 105, it may expel air as needed even when the residual limb is nearly fully, or fully, inserted into the socket. Also, in this area, the valve system 10 is discreet when covered by clothing and does not protrude (as it would from a more proximal side of the socket) to catch on clothing or other items.

After the base 20 is attached to the hard socket 105, preferably by adhesive, a hole 125 is drilled through the sidewall 110 of the hard socket 105 via the bore 22 in the base 20, so that the hole 125 generally aligns with the interior bore 22, and bore 32 and opening 62 discussed below, for fluid communication between the socket well, hole 125, bores 22, 32 and opening 62 to vent air out of the socket interior I.

One may see from the drawings that the preferred valve 10 has base 20, o-ring 40, valve housing 30, stem 50 and ring/cover 60 all being coaxial, creating a passageway or "exit path" for air to pass through when the one-way valve opens. Note that, when fully assembled, the ring/cover 60 may snap into housing 30 (so that it can be easily removed for cleaning of the system) or may be attached to housing 30 by other methods such as adhesive.

In use, when the air pressure inside the hard socket 105 (between the liner-covered residual limb and the socket interior surface) exceeds the desired air pressure, as further discussed below, the air will force the valve stem 50 to move away from the opening 125 in the hard socket 105, compressing the spring 55 against the ring 60. This movement of the stem 50 unseats the end 54 of the stem from the sealing surface 38, allowing air to flow around the end 54 and along the sides of the stem to the opening 62 of the ring, and out to the ambient air.

In other words, the valve system 10 comprises the valve assembly 11 that is inserted into the base 20, which valve assembly 11 comprises a valve housing 30 having an internal circular bore 32 with a conical sealing surface 38 and an external threaded portion 34. The threaded portion 34 on the valve housing 30 has a slightly smaller diameter than the threaded bore 22 in the base 20, so that it may cooperate with the threaded bore 22 in the base 20. As explained above for the base 20, the valve housing 30 may be otherwise adapted for connecting/securing to the base. For example, the valve housing may not have any threads and may instead have bayonets that are received in slots in the base when the valve housing is inserted into and rotated in the base.

The exterior of the valve housing 30 is shown as "hex-shaped," but other shapes may be used, such as other polygonal shapes or a cylindrical shape. The hex-shape is preferable as it may allow the technician to easily install and tighten the valve housing or the entire assembly in the base. Also, because the hex-shape provides a good surface to grip, it may allow the user to manually open the valve, in effect by disassembling the valve (removing the valve assembly from the base), if necessary, prior to the user removing his/her residual limb from the hard socket 105.

An o-ring 40 or other seal is placed in a recess in the base 20 between the base 20 and the valve housing 30. Once the valve housing 30 is threadably or otherwise received and secured in the base 20, an air tight seal is created between the base 20 and the housing 30.

The valve assembly 11 further comprises a valve stem 50 received in the bore 32 of the housing 30. The valve stem 50 slides axially inside the bore 32 to seat against the sealing surface 38 of the housing, when the valve is closed, and to move away from and unseat from the sealing surface 38 when the valve is open. A spring 55 biases the valve stem 50 into the closed, seated position to close the valve except when a differential air pressure overcomes the spring 55 bias and pushes the valve stem 50 away from the sealing surface. Spring 55 is preferably a cylindrical coil compression spring, the design of which is the main determining factor in the crack pressure of the valve and which one of average skill can design after reading this disclosure.

The valve assembly, including the bias spring 55, are adapted so that a differential pressure selected from a certain amount will "crack" or "pop" open the valve. In other words, the valve assembly and particularly the spring 55 are preferably designed so that, when the pressure on the "inner side" of the valve (to the left in FIGS. 5 and 6, and typically on the inside of the socket between the liner-covered limb and the interior surface of the socket at the lower end of the socket) is a certain amount above the pressure on the "outer side" of the valve (to the right in FIGS. 5 and 6, and typically outside the socket), then the valve will open. This "certain amount" is preferably in the range of 1-3 psi, and more preferably in the range of 1-2 psi. As soon as the differential pressure drops (that is, as soon as the inner pressure is less than the predetermined amount, preferably 1-3 psi or 1-2 psi, higher than the outer pressure) the spring 55 will again bias the valve stem 50 to the closed, seated position. Thus, as discussed above, the valve will open, if necessary, with each step of the wearer's gait, to allow air to vent from the socket well, and then quickly close after the air has been vented and/or when the swing portion of the gait lowers the pressure inside the socket well.

The valve stem 50 preferably has an internal bore 52 (or other hollow or recessed end or cavity that opens to the housing bore preferably at the spring-end of the valve) that may receive air that is flowing out of the valve in the "exit path" comprising passing around the stem, through or around the spring, and out through the outer end of the valve (at ring 60). Internal bore 52 may provide extra space for this flowing air, as it passes around or through the spring to exit the valve, thus helping prevent unpleasant noise or venting sounds that might occur with too-narrow portions of the exit path. Further, various embodiments of the bore 52 may be advantageous during the molding or machining process, for weight reduction, and/or for cooperating with or connecting to a spring or other bias member. The preferred location of the spring 55 places the spring between the flat face 53 of the valve stem 50 and the inner face 63 of the ring 60, and held there securely enough that it may be repeatedly compressed between those surfaces and then released, when the valve opens and closes, respectively, without significantly shifting from its preferred radially-centered position.

Further, as shown in FIG. 8, there may be an o-ring 58 or other material on the generally conical end 54 of the stem 50, which o-ring 58 or other material is preferably a softer or more flexible material, compared to the preferred brass or hard plastic valve stem 50, for enhancing the seal between the stem 50 and the sealing surface 38. Alternatively, the entire stem 50, the conical end 54 of the stem, or another portion of the stem may be made of a softer plastic or other material with enhanced sealing performance.

Retaining ring 60 is a generally thin disc that is friction-fit, snapped, or otherwise secured and anchored into the bore 32 of the housing 30 to retain the spring 55 and the stem 50 in their proper positions inside the housing. The ring 60 is preferably secured to the housing, on ledge 39, in such a way that it will not normally come out of the housing, but that an external prosthesis technician could pry or otherwise remove it to clean the valve assembly 11 and/or replace parts of the valve assembly 11. Ring 60 has an opening 62 through which the air is expelled. Alternative ways of retaining the valve stem, spring, and/or other parts as may be desired, in the housings of the valve may be used.

The preferred stem 50 is a hexagonal, or other polygonal shape, so that it has multiple flat or generally flat sides 56. Therefore, the air may flow along the end 54 of the stem and through the bore 32 of the housing in between the housing inner surface and one or more of the flat sides 56. This provides multiple passages for the air, with each preferably being a relatively wide passage (that is, radially wider than if the stem where cylindrical inside a cylindrical housing bore), which is believed to be important for reducing air-venting noise. These passages may be said to be "spaced gaps"

between the stem and the housing, in that they are spaced apart (separated) by the edges 57 of the stem, which contact, or come very close to, contacting the bore 32 surface. These gaps, therefore, may also be called non-annular gaps or non-annular spaces, as the gap/space between the stem and the bore of the housing is preferably not simply a continuous, annular space around the entire stem, but rather multiple axial passageways that are separated/spaced apart by the edges 57 that are close to, or that contact, the bore 32. It may also be said that, because the stem and the housing bore are not the same shape (and particularly not the same circumferential shape), there are multiple gaps between the stem and the housing bore created by this difference in shape. This also places the stem 50 in the housing in a slidable arrangement, where it slides axially in the housing bore 32, with contact being between the edges 57 of the sides 56 and the bore 32 surface, but not all the way around the circumference of the stem. This may be important for keeping the stem freely slidable in the bore 32 and less prone to plugging, seizing and/or becoming fouled to an extend that the valve would make more noise.

The preferred combination of an axially-sliding stem, and a polygonal or other stem shape, that provides multiple air passages along the sides of the stem (which are relatively wide by being flat, recessed, or otherwise spaced from the preferably cylindrical housing bore wall) are believed to be at least part of the reason for the quiet, consistent, and effective operation of the valve. Also, the preferred low crack pressure that is achievable with the preferred valve with repeated, consistent operation, is believed to be important and beneficial for quiet operation and effective prosthetic suspension without large swings in socket pressure.

Preferably, the base 20, valve housing 30, and retaining ring 60 are fabricated from a light-weight durable material, for example, Delrin™ plastic; however, other materials may be used such as aluminum, titanium, nylon or other plastics. Additionally, the stem 50 may be hard plastic or brass, but also may be manufactured from other materials, for example, including other metals, plastics, or combinations thereof.

The preferred valve system 10 is adapted to be fitted on the outside surface 115 of the hard socket 105, and most preferably only to the outside surface 115. The valve system 10 is preferably attached with adhesive, by applying adhesive of types known in the field of prosthetic sockets to the bottom 24 of the base and/or to the outer surface 115. Other securement means may be used, but adhesive is preferred as it has been found to be reliable, easy to use, and not requiring any other fasteners or complex or protruding parts. Preferably, no portion of the valve system 10 extends through the socket wall, or into the interior space I of the hard socket 105, or contacts the inside surface 120 of the hard socket 105. The opening/hole 125 in the socket wall is made by drilling or otherwise cutting through the socket wall, and this step preferably does not include any threading or other shaping or preparing of the socket or the hole therein. Thus, the preferred valve and attachment of the valve may be used effectively with modern thin-walled, light-weight sockets. The valve system 10, in the preferred but not all embodiments, consists essentially only of, and may consist only of, a base, a valve housing, an o-ring or other seal, a stem with or without supplemental sealing member or portion, a spring and a retainer ring or other closure or cover. This simple design is effective in terms of manufacture, installation, and operation, and has many benefits over prior art valves, including over the prior art valves that are more complicated, prone to plug-up, prone to make venting noise, that include ball-and-spring systems, and/or that screws/threads into the socket wall and/or that resides on both sides of the socket wall. In the preferred embodiment of the invented valve system, only the base, and more preferably only its bottom surface (24) or portions of the bottom surface (24), is in contact with the hard socket.

Preferred embodiments may be described as a one-way pressure-control system for a prosthetic hard socket, wherein the prosthetic socket comprises a wall having an outer surface and an interior surface defining a well for receiving a residual limb, and said wall has a hole extending from said outer surface to said interior surface; and wherein the valve system comprises: a base connected to said outer surface and having a base bore positioned over said hole in the wall; and the valve housing being connected to said base and extending into said base bore and having a housing bore generally coaxially aligned with said base bore and in fluid communication with said hole in the socket wall, said valve housing having a sealing surface; a valve stem received in said housing bore and slidable into a first, sealed position wherein a portion of said valve stem (preferably a sealing end) seals against said sealing surface and into a second, unsealed position away from the sealing surface; and a spring biasing the valve stem into the first, sealed position until said air pressure inside the prosthetic socket well is at a differential pressure in the range of 1-3 psi greater than ambient pressure outside the socket, at which time the valve stem is pushed by said differential pressure into said second, unsealed position so that air leaves the socket well by flowing through the hole and through the valve system. Alternatively, or in addition, the valve stem circumference may be not the same shape as the housing bore circumference (preferably one of the two being non-circular) so that, when the valve stem is in the second, unsealed position, air flows around the valve stem through axial gaps between the valve stem and the housing. Preferably, this difference in circumference/shape occurs along the stem side portion, which is the side portion of the stem not adapted to contact the sealing surface. The axial gaps are preferably different from simply an annular space all the way around the stem, and, instead, are axial passages separated by edges that come close to, or touch the housing bore. These edges' proximity to the housing bore wall keeps the valve stem generally centered in the housing bore, while air flows freely past the valve stem through said axial gaps. Thus, the valve stem may be described as being shaped so that multiple axial gaps between the stem and a stem housing extend along the length of the valve stem to receive air flow when the valve stem is in the second, open position, and so that said multiple axial gaps are separated by axial edges of the valve stem that contact or come close to said stem housing and keep said valve stem generally centered in said housing. In many embodiments, said valve stem further has a hollow end with an opening near said spring, wherein said opening is in communication with the air passageway(s) through the valve, providing additional space for air to flow or reside, further reducing air venting noise. The venting of air sooner (at lower differential) and with less-restricted flow, compared to prior art vents is believed to be instrumental in reducing or eliminating the sudden, louder pop, squeak, or sputtering sounds of prior art devices.

The invention may also comprise the methods of installing and using such a valve system. For example, some embodiments of the invention may comprise a method of installing a pressure-relief valve in a prosthetic socket, wherein the method comprises: providing a hard socket; providing a one-way air valve comprising a base with a base bore, a removable valve stem housing with a housing bore, valve stem, and a spring; adhesively attaching said base to the outside of the socket; drilling a hole through the socket by inserting a drill bit through said base bore and drilling through the socket to make a hole in the wall generally coaxially aligned with said bore in the base; inserting and securing said housing into the base so that the housing bore is generally coaxially aligned with said base bore and said hole in the wall; inserting the valve stem and spring into the housing bore so that said valve stem slides in the housing bore to a closed position and an open position to allow venting of air out of the socket well when pressure builds in the socket to a differential pressure that is greater than ambient pressure. Preferably, the method comprises no insertion of any part of the air valve into the socket well, and no part of the air valve extends through the socket wall to reach the well. Preferably, the only attachment of the air valve to the socket is adhesive connection of the base to the outer surface of the socket, and, preferably, there is no threaded attachment of the air valve to the socket.

Referred now to FIGS. 9-11, an alternative embodiment comprises a valve unit 110 that includes a manual valve as well as a one-way valve. From the cross-sectional view of FIGS. 9 and 10, one may see that the one-way valve assembly 111 is threadably connected to a handle 120 that generally serves the same purpose relative to the valve assembly 111 as base 20 serves to valve assembly 11, however, handle 120 is not directly attached to the socket. Instead, handle 120 is preferably expanded in diameter and/or provided with a flared outer circumference portion, or grip portion 121, of hexagonal or other polygonal shape, to provide the user a larger, and preferably easily-rotatable grip surface when operating the manual valve. Further, instead of having a flat bottom (or rear surface) that attaches directly to the hard socket, handle 120 has a rear protrusion 123 that is received in and operatively connected to base 170. It is base 170 that is directly connected to the socket, preferably in the same way as discussed above for the base 20, that is, by adhesive. As discussed in detail for base 20, base 170 preferably does not connect to, or include, any structure that reaches through the socket wall or into the socket well, but rather firmly is glued/adhesively attached to a distal region of the socket exterior wall surface. As discussed with base 20, a hole (H in FIGS. 9-11, 14, 15) may be drilled through the socket wall after attachment of the base 170 to the socket, or by other means or steps. As may be understood from discussion of such an attachment, it will be understood that such an attachment will be effective for a thin-walled socket and will be convenient and simple compared to more complex mechanisms that require fasteners or clamps or other structure both on the inside and the outside of the wall.

The operative connection of handle 120 (preferably with its valve assembly 111 including valve casing 111') and the base 170 allow said handle and base to form a manual valve system that is substantially or entirely independent of the operation of the one-way valve. Handle 120 is preferably rotatable relative to base 170, and is preferably coaxial with the base 170. Upon rotation, in one direction, the handle 120 move close to the base 170 to seal against the base, and, upon rotation in an opposite direction, the handle 120 moves out away from the base 170 to create a space between the handle and base that allows air flow between the handle and base. In the manual valve closed position, shown in FIGS. 9 and 10, the rear surface 124 of the handle grip portion 121 seals to the front flange 172 of the base 170, most preferably by means of an o-ring or gasket 174 provided in a groove on the flange 172 or otherwise retained on the flange. One may see in FIGS. 9 and 10 that the one-way valve assembly 111 may operate as described above for valve assembly 11 (closed in FIG. 9 and "popped" open in FIG. 10) when the manual valve system is closed, that is, when the handle 120 and base 170 are in closed, sealed condition. When the manual valve is closed, the only passageway possible for air exit through the valve 110 is to pop the one-way valve. It is noteworthy that, whether the manual valve is closed, air may pass through the base 170 (through bore 176) and through the rear aperture 125 in the rear protrusion 123 to reach the one-way valve stem 150, and, upon opening the stem 150 (as discussed above for stem 50), the air may flow around the stem and out of the one-way valve assembly via opening 162. When the manual valve is opened, as discussed below, air will flow out via the space/gap between the base 170 and the handle 120, rather than popping the one-way valve, or will flow in via said space/gap, depending upon the relative pressures inside the socket and outside the socket.

The preferred method of operating the manual valve is by rotation of the handle 120 relative to the base 170, wherein cooperating structure of the handle and base serves to distance the handle 120 from the base 170 upon at least a portion of said rotation. Said cooperating structure preferably comprises at least one ramp on either of said handle 120 or said base 170 and at least one riding member on the other of said handle or base, wherein relative rotation of the handle and base allow the riding member to "ride" or slide along the ramp to change the relative axial location of the handle and the base. Said at least one ramp is slanted so that rotation preferably in the range of 30-270 degrees (more preferably 30-90 degrees and most preferably 30-70 degrees) distances the handle from the base enough to unseal the two from each other for air flow there-between. The riding member may be a protrusion or ramp. When the riding member is itself a ramp, one may consider the ramps to cooperate as do threads, but only threads that allow less than a full rotation. In other words, the handle may be unscrewed from the base less than a full rotation, so that the handle movement has an axial component to move the handle slightly out from the base. The rotational operation of the valve, in each of the opening direction and the closing direction, preferably is only a partial rotation (30-270 degrees, more preferably, a partial rotation in the range of 30-90 and, most preferably 30-60, degrees). Opening by rotation in the range of about 30-60 degrees, and closing in the opposite direction by rotation the same amount (also in the range of 30-60 degrees) is particularly comfortable and easy to perform, as the user simple "twists" the handle a short distance one way and then the other. The especially-preferred operation, therefore, is more like a quick twist than an screwing/unscrewing a threaded system.

In the especially-preferred embodiment, two ramps 127, 129 are provided 180 degrees apart on the outer, cylindrical surface 134 of the rear protrusion 123. Two tabs 177, 179 are provided on the interior cylindrical surface of the bore through base 170, and extending between the tabs 177 179 on said interior surface are ramps 181, 182. When the preferred handle 120 is rotated clockwise relative to the preferred base 170, ramps 181, 182 ride along ramps 127, 129 to pull the handle closer to the base, as if the handle were being screwed into the base, to an extent that seals the handle to the base at o-ring/gasket 174. When the preferred handle 120 is rotated counterclockwise relative to the preferred base 170, ramps 181, 182 ride in the opposite direction along ramps 127, 129 to allow the handle to be slightly distanced from the base, as if the handle were being unscrewed part-way from the base, to an extent that unseals the handle from the base at o-ring/gasket 174. In this open condition, as shown in FIG. 11, air may flow out from the socket or into the socket through the space S (space S shown in FIG. 15) between the handle and the base.

Tabs 177, 179 move, during said rotation, preferably between limiting structure (L, FIGS. 16 and 17) that is preferably at the ends of ramps 127, 129. The tabs 177, 179 may move between said limits L in areas of the outer surface 134 that is recessed relative to the areas upon which the ramps 127, 129 are located.

The handle 120 and base 170 are preferably connected and disconnectable by means of a snap system, wherein the handle snaps into the base and then is rotatable relative to the base. In the preferred embodiments, the handle and base snap together by the handle being positionable relative to the base in a position wherein portions of the ramps 181, 182 and/or tabs 177, 179 snap over slightly-protruding structure on the outer, cylindrical surface 134 to a point wherein the handle is base is held on the handle. Preferably, spaces (significantly wider than the tabs 177, 179) exist between the two ramps 127, 129 on the surface 134 (said relatively recessed areas mentioned above) and, as the two tabs 177, 179 into those recessed spaces, slide, portions of ramps 181, 182 also slide into said spaces and portions of ramps 181, 182 snap over the cooperating ramps 127, 129 on the handle rear protrusion outer surface 134. There may be an optional slight protrusion at the entry of the recessed spaces over which the tabs may snap. When the tabs slide into the recessed spaces and the ramps 181, 182 snap over ramps 127, 129, the base ends up in a position relative to the handle wherein the base is close to, and generally tight against the handle, and the manual valve is therefore closed. In this position, the handle and base have snapped together, and are in position for the ramps to slide along each other to open the manual valve when the handle is twisted counterclockwise relative to the base. If substantial pulling on the handle were conducted, the handle might snap off of the base, this is unlikely to happen unintentionally, as only twisting is necessary, and not pulling or pushing, to open and close the manual valve.

In FIGS. 12-15, and 18, there is shown yet another embodiment 210, wherein the valve system 210 comprises only a manual valve and not a one-way air outlet valve. The valve system 210 may be the same as that described above for FIGS. 9-10, but, instead of the handle having a bore there-through that receives and cooperates with a one-way valve assembly, the handle 120' is closed at its front (toward the right in FIGS. 12-15, and 18. The handle may still have a front, central indent, as portrayed in FIGS. 14 and 15, but this is preferably simply an optional indent or depression. As in the embodiment of FIGS. 9-11, the embodiments of FIGS. 12-15 and 18 allows air to flow out of, and into, the socket, by flowing axially through a portion of the passageway (the portion in the base) and radially (through the space between the flange of the base and the rear side of the rear protrusion 123 of the handle.

The hard socket is preferably chosen from many conventional rigid prosthetic sockets currently available on the market. The suspension and/or connection systems for connection the hard socket may include locks, straps, and other mechanisms that are available on the market.

Although this invention has been described above with reference to particular means, materials and embodiments, it is to be understood that the invention is not limited to these disclosed particulars, but extends instead to all equivalents within the broad scope of the following claims.

The invention claimed is:

1. A pressure-control system for a prosthetic hard socket, the pressure-control system comprising:
   a prosthetic socket comprising a wall having an outer surface and an interior surface defining a well for receiving a residual limb, and said wall having a hole extending from said outer surface to said interior surface; and
   a valve system comprising:
      a base connected to said outer surface and having a base bore positioned over said hole in the wall;
      a handle connected to said base by a rear portion of the handle snapping into the base and having a handle bore generally coaxially aligned with said base bore and in fluid communication with said hole in the socket wall;
      a valve casing connected to said handle and having a casing bore generally coaxial, and in fluid communication, with said handle bore and said base bore;
      a valve stem slidably received in said casing bore and slidable into a first, sealed position wherein a portion of said valve stem seals against a sealing surface of the valve casing and into a second, unsealed position away from the valve casing sealing surface; and
      a spring biasing the valve stem into the first, sealed position until said air pressure inside the prosthetic socket well is at a differential pressure in the range of 1-3 psi greater than ambient pressure outside the socket, at which time the valve stem is pushed by said differential pressure into said second, unsealed position so that air leaves the socket well by flowing through the hole, the base bore, the handle bore, and the casing bore;
      wherein the handle is rotatable in a first direction a portion of a full rotation in the range of only 30-90 degrees relative to the base to an open position forming a radial gap between said base and said handle, so that air from the socket well passes axially through the hole and the base bore, and radially through said radial gap, wherein rotation of said handle 30-90 degress relative to the base forms said radial gap by means of two handle ramps provided on an outer surface of the rear portion of the handle sliding relative to two cooperating base ramps provided on an inner surface of the base, said two handle ramps being spaced 180 degrees apart on said outer surface of the rear portion of the handle, and said two handle ramps and said two base ramps being slanted so that the handle rotating said 30-90 degree portion of a full rotation moves the handle axially out from the base to form said radial gap; and
      wherein said valve system comprises a limit mechanism at each end of each of said two handle ramps and a tab at an end of each of said two base ramps, wherein the limit mechanism and the tabs prevent said handle from rotating in said first direction more than said 30-90 degree portion of a full rotation.

2. A pressure-control system as in claim 1, wherein said valve stem is non-cylindrical.

3. A pressure-control system as in claim 1, wherein said valve stem is non-circular in radial cross-section.

4. A pressure-control system as in claim 2, wherein said valve stem is polygonal.

5. A pressure-control system as in claim 1, wherein said base is adhesively attached to the socket and no part of the valve system extends through the socket into the well of the socket.

6. A pressure-control system as in claim 1, wherein said handle has a polygonal exterior surface.

7. A pressure-control system as in claim 1, wherein said portion of a full rotation is in the range of 30-90 degrees.

8. A pressure-control system as in claim 1, wherein: said valve stem has a valve stem circumference and said valve casing has a casing bore circumference, and wherein said valve stem circumference is not the same shape as the casing bore circumference, and one of said casing bore circumference or said valve stem circumference is non-circular, so that, when the valve stem is in the second, unsealed position, air flows around the valve stem through axial gaps between the valve stem and the valve casing.

9. A pressure-control system as in claim 8, wherein said valve stem is polygonal and the casing bore is cylindrical.

10. A pressure-control system as in claim 8, wherein no part of the valve system extends through said socket wall into the socket well.

11. A pressure-control system as in claim 8, wherein said base is adhesively attached to the socket and no part of the valve system extends through the socket into the well of the socket.

12. A pressure-control system as in claim 8, wherein said casing housing has a polygonal exterior surface.

13. A pressure-control system as in claim 8, wherein said valve stem has a hollow end that receives a portion of said spring.

* * * * *